US009888945B2

(12) United States Patent
Walters et al.

(10) Patent No.: US 9,888,945 B2
(45) Date of Patent: Feb. 13, 2018

(54) SYSTEMS AND METHODS FOR CORRECTING SPINAL DEFORMITY

(71) Applicant: Alphatec Spine, Inc., Carlsbad, CA (US)

(72) Inventors: Carmen Walters, Carlsbad, CA (US); Ketchen Smith, Escondito, CA (US); Benjamin Walter Wang, Carlsbad, CA (US)

(73) Assignee: Alphatec Spine, Inc., Carlsbad, CA (US)

(*) Notice: Subject to any disclaimer, the term of this patent is extended or adjusted under 35 U.S.C. 154(b) by 0 days.

(21) Appl. No.: 14/331,579

(22) Filed: Jul. 15, 2014

(65) Prior Publication Data
US 2016/0015427 A1 Jan. 21, 2016
US 2017/0189072 A9 Jul. 6, 2017

Related U.S. Application Data

(63) Continuation of application No. 13/367,602, filed on Feb. 7, 2012, now abandoned.

(60) Provisional application No. 61/440,640, filed on Feb. 8, 2011.

(51) Int. Cl.
*A61B 17/70* (2006.01)

(52) U.S. Cl.
CPC ...... *A61B 17/7025* (2013.01); *A61B 17/7014* (2013.01); *A61B 17/7043* (2013.01)

(58) Field of Classification Search
CPC ................................ A61B 17/7049–17/7052
USPC .................................................. 606/250–253
See application file for complete search history.

(56) References Cited

U.S. PATENT DOCUMENTS

| | | | |
|---|---|---|---|
| 6,355,038 B1* | 3/2002 | Pisharodi | A61B 17/7043 411/538 |
| 2005/0171543 A1* | 8/2005 | Timm | A61B 17/7007 606/257 |
| 2006/0271050 A1* | 11/2006 | Piza Vallespir | A61B 17/7085 606/86 A |
| 2009/0264926 A1* | 10/2009 | Taylor | A61B 17/7041 606/246 |
| 2010/0094345 A1* | 4/2010 | Saidha | A61B 17/7049 606/250 |
| 2012/0203279 A1* | 8/2012 | Walters | A61B 17/7077 606/252 |

* cited by examiner

*Primary Examiner* — Nicholas Plionis
(74) *Attorney, Agent, or Firm* — Dinsmore & Shohl LLP

(57) ABSTRACT

An exemplary system for correcting a spinal deformity includes a plurality of transverse rods, a longitudinal rod, and at least one node. The plurality of transverse rods each includes a first end for coupling with an extension member of a spinal fixation system and a second end. The longitudinal rod extends transverse to the transverse rods. The at least one node receives the second ends of first and second transverse rods and the longitudinal rod within a receiving portion and an adjustment member selectively secures the second ends.

5 Claims, 9 Drawing Sheets

SYSTEMS AND METHODS FOR CORRECTING SPINAL DEFORMITY

CROSS-REFERENCE TO RELATED APPLICATIONS

This application claims priority to U.S. Provisional Application Ser. No. 61/440,640 filed on Feb. 8, 2011 and incorporated herein by reference in its entirety.

FIELD

The present disclosure generally relates to the field of spinal orthopedics, and more particularly to systems and methods for correcting spinal deformities.

BACKGROUND

The spine is a series of individual bones called vertebrae, separated by cartilaginous disks. The spine includes seven cervical (neck) vertebrae, twelve thoracic (chest) vertebrae, five lumbar (lower back) vertebrae, and the fused vertebrae in the sacrum and coccyx that help to form the hip region. While the shapes of individual vertebrae differ among these regions, each is essentially a short hollow tube containing the bundle of nerves known as the spinal cord. Individual nerves, such as those carrying messages to the arms or legs, enter and exit the spinal cord through gaps between vertebrae. The spinal disks act as shock absorbers, cushioning the spine, and preventing individual bones from contacting each other. Disks also help to hold the vertebrae together. The weight of the upper body is transferred through the spine to the hips and the legs. The spine is held upright through the work of the back muscles, which are attached to the vertebrae. While the normal spine has no side-to-side curve and rotational misalignment, it does have a series of front-to-back curves, giving it a gentle "S" shape. If the proper shaping and/or curvature are not present due to scoliosis, neuromuscular disease, cerebral palsy, or other disorder, it may be necessary to straighten or adjust the spine into a proper curvature and alignment.

Generally the correct curvature and alignment are obtained by manipulating the vertebrae into their proper position and securing that position with screws and rods. The rods which are shaped to mimic the correct curvature and force the spine into proper alignment. Bone grafts are then placed between the vertebrae to aid in fusion of the individual vertebrae together to form a correctly aligned spine.

Spinal deformity correction procedures can require complex anatomical manipulation to restore proper anatomic form to the patient. Currently, some systems have non-linkable tubes with handles to perform vertebral column manipulation (VCM). VCM with a rotational force applied on bone anchors in the coronal plane (medial-laterally) is referred to as "derotation". Because correction of a large, complex 3-dimensional spinal deformity can exert a high stress concentration on the bone anchor element and anatomy, forces should be distributed between multiple levels and multiple bone anchors in order to reduce the occurrence of anatomical damage (i.e. screw breach through the vertebrae).

SUMMARY

An exemplary system for correcting a spinal deformity includes a plurality of transverse rods, a longitudinal rod, and at least one node. The plurality of transverse rods each includes a first end for coupling with an extension member of a spinal fixation system and a second end. The longitudinal rod extends transverse to the transverse rods. The at least one node receives the second ends of first and second transverse rods and the longitudinal rod within a receiving portion and an adjustment member selectively secures the second ends.

In other features, another node receives the second ends of third and fourth transverse rods and the longitudinal rod within another receiving portion and another adjustment member selectively secures the second ends. Each second end includes a rounded portion that pivots within a receiving portion of the node that includes one or more rounded recesses configured to receive the rounded portion. The adjustment member provides clamping force on an upper portion and a lower portion of the receiving portion to secure the transverse rods. Each first end includes a linking member that couples with the extension member. The linking member includes a first aperture that receives the first end and a second aperture that couples with the extension member.

In still other features, an alignment clip includes a pair of arms that extends around a first extension member of a first vertebral level and a second extension member of a second vertebral level to enable simultaneous movement of the first and second vertebral levels. The alignment clip includes an aperture for receiving one of the first extension member and the second extension member. The alignment clip includes a pin at a first end and a locking mechanism at a second end that selectively locks the pair of arms together. An inter-level connector includes a first coupling mechanism that attaches to the pair of arms and a second coupling mechanism for attachment to each first end of the transverse rods.

Another exemplary system for correcting a spinal deformity includes a plurality of transverse links and a plurality of linking arms. Each transverse link includes an adjustable length, a plurality of attachment points along the adjustable length, and first and second apertures for receiving first and second extension members of a spinal fixation system. Each linking arm includes a first mating feature that attaches to a first attachment point of a first transverse link and a second mating feature that attaches to a second attachment point of a second transverse link In other features, each transverse link includes a first plate that slidably receives a second plate. Each linking arm attaches to adjacent first and second transverse links Each of the first and second apertures includes a rounded inner surface configured to receive a sleeve having a mating rounded outer surface. The attachment points and mating features include at least one of a peg, a pin, a slot, and an aperture.

An exemplary method of correcting a spinal deformity includes coupling a first end of a first transverse rod with a first extension member of a first vertebral level of a spinal fixation system, coupling a first node with a second end of the first transverse rod, coupling a first end of a second transverse rod with a second extension member of the first vertebral level of the spinal fixation system, and coupling the first node with a second end of the second transverse rod.

In other features, the method includes coupling a first end of a third transverse rod with a first extension member of a second vertebral level of the spinal fixation system, coupling a second node with a second end of the third transverse rod, coupling a first end of a fourth transverse rod with a second extension member of the second vertebral level of the spinal fixation system, and coupling the second node with a second end of the fourth transverse rod.

In still other features, the method includes inserting a longitudinal rod extending transversely to the transverse rods through the first node and the second node; rotating at least one of the second ends of the first, second, third, and fourth transverse rods within recesses formed in at least one of an upper portion and a lower portion of at least one of the first and second nodes; and adjusting a clamping force on the upper portion and the lower portion of at least one of the first and second nodes to secure the second ends therebetween.

DETAILED DESCRIPTION

The systems and methods of this disclosure relate to a structural system which aids a surgeon in manipulating vertebrae in a spinal fusion procedure. Variations of the system may include one or more of the following: extension members, extenders, transverse links, extension member remover instruments, derotation instruments, alignment clips, rod reducers, alignment nodes, transverse rods, longitudinal rods, and other components.

The systems and methods of the present disclosure allow a surgeon to selectively maneuver two or more vertebrae at a time. The system allows multiple vertebral levels to be coupled together both cephalad-caudally and contra-laterally. Coupling of the bone anchors allows VCM forces to be distributed across multiple levels and bone anchors thereby increasing the safety and efficacy of the deformity correction procedure. Additionally, the derotation tubes will function as axial rod reducers to allow for both active clamping onto the bone anchor element and rod reduction.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

Figure 1:
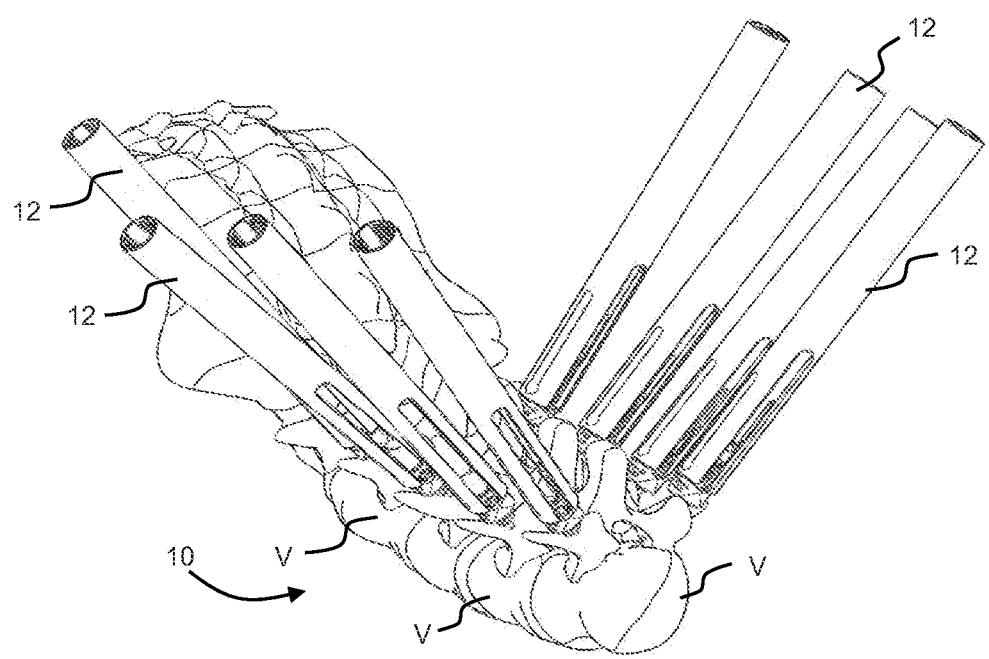
FIG. 1 is a perspective view of a screw extender system attached to a spinal column.

Referring to FIG. 1, a portion of an exemplary spinal column 10 is shown. The spinal column 10 includes numerous vertebrae V including, lumbar, thoracic, and cervical vertebrae. Although the portion depicted primarily includes vertebrae of the lumbar region, the present disclosure relates systems and methods for any region of the spinal column 10. The vertebrae V are instrumented with screws (not shown) and extension members 12 such as screw extenders, derotation towers, and the like as known in the art. The extension members 12 may function as derotation tubes or extension members to provide leverage to align the vertebrae and facilitate insertion of fixation rods. Exemplary screws and extender systems may be found in U.S. Patent Pub. No. 2010/0036443. The screws may include polyaxial screws having threaded shafts and rounded heads. The screws may be attached to the pedicles of the vertebrae and polyaxial body members attached to the heads. The body members receive the fixation rods to rigidly secure the vertebrae for fusion. The extension members 12 may removably attach to the body members of the screws and provide leverage to manipulate the vertebrae prior to fusion. The extension members 12 may also include slots for insertion of the fixation rods.

Figure 2:
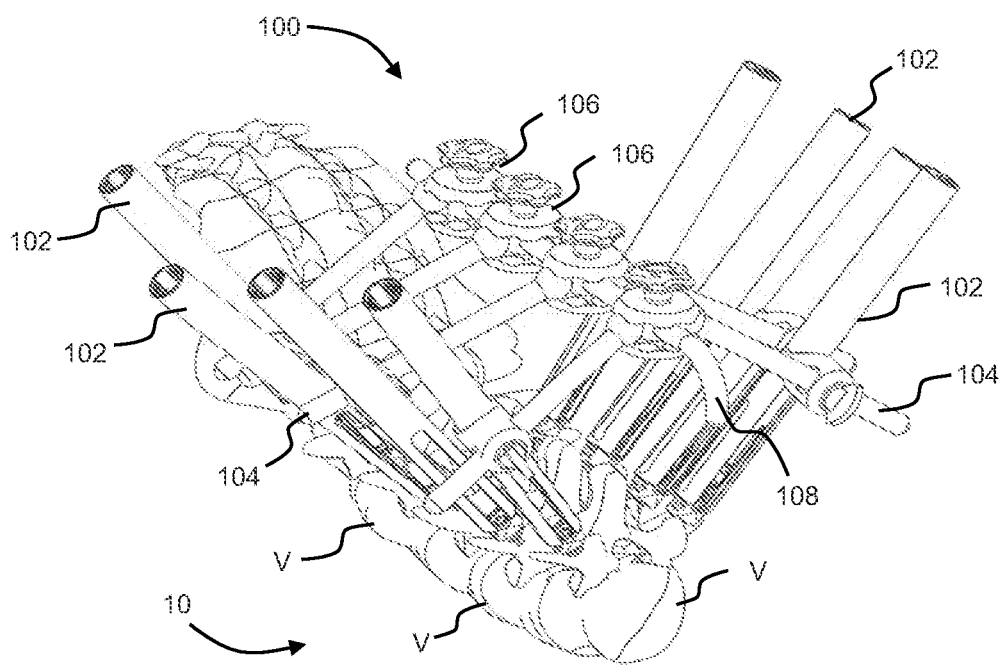
FIG. 2 is a perspective view of one example of a system for correcting spinal deformities as attached to the screw extender system according to the principles of the present disclosure.

As shown in FIGS. 1 and 2, in one embodiment, a system 100 for alignment of the spine 10 may be used with one or more screws installed in the pedicles of the vertebral bones. In this embodiment, extension members 102 are attached to the pedicle screws. The extension members 102 may attach in various ways such as with opposing mating protrusions, clip-on, snap-on, spring-biased attachment, or threaded attachment. The extension members 102 may include the extension members 12 as described above. The system 100 may include a plurality of transverse alignment rods 104, a plurality of alignment nodes 106, and a longitudinal alignment rod 108.

Figure 3:
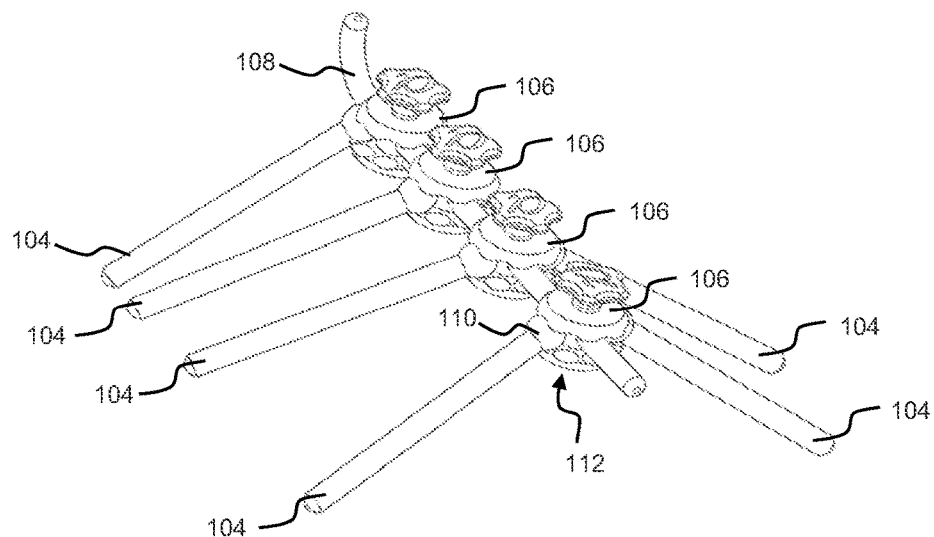
FIG. 3 is a perspective view a portion of the system for correcting spinal deformities according to the principles of the present disclosure.

Continuing now also with FIG. 3, the transverse rods 104 may be substantially cylindrical from a first end proximate to the extension members 102 to a second end proximate to the longitudinal alignment rod 108. The second end may form an end portion 110, such as a rounded or spherical portion, that permits rotation and pivoting of the transverse rod 104 relative to the node 106. The alignment nodes 106 may be substantially cylindrical or spherical and include receiving portions 112 for receiving the end portions 110 of the transverse rods 104. The longitudinal rod 108 generally runs parallels to the spine 10 and transversely to the transverse rods 104. The longitudinal rod 108 may be a singular rod or alternate means for stabilizing and connecting the nodes 106 to make a cohesive unit from the multiple alignment nodes 106.

Figure 4A:
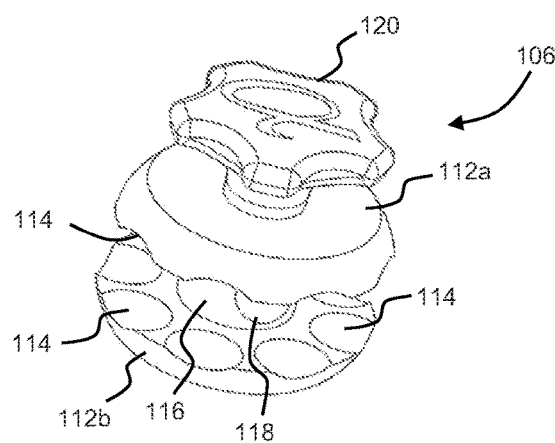
FIGS. 4A and 4B are perspective views of an exemplary node of the system for correcting spinal deformities according to the principles of the present disclosure.
Figure 4B:
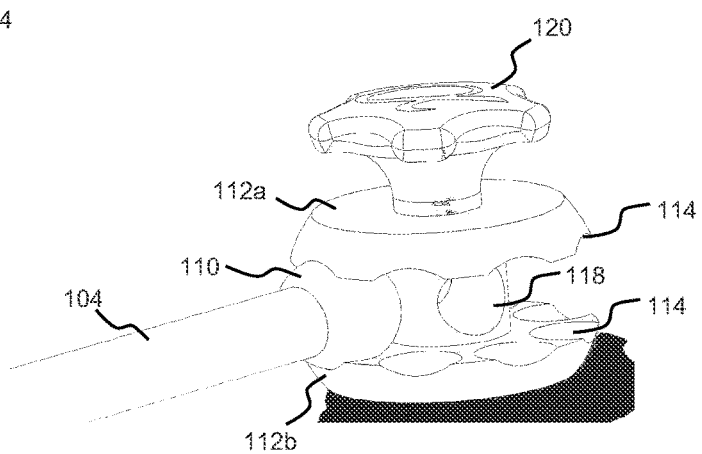

Referring now to FIGS. 4A and 4B, one of the nodes 106 is shown in greater detail. The receiving portion 112 of the node 106 may include a first upper portion 112a and a second lower portion 112b. The receiving portion 112 may include one or more recesses 114 configured to secure the end portion 110 of the alignment rod. For example, in the present embodiment, the recesses 114 include hemispherical profiles that conform to spherical profiles of the end portion 110. Thus, the transverse rods 104 may freely rotate due to a ball and socket joint formed by the recesses 114 and end portion 110. A linking member 116 links the upper portion 112a and lower portion 112b together and may include internal springs (not shown) to bias the upper portion 112a and lower portion 112b apart from one another. An aperture 118 in the linking member 116 receives the longitudinal rod 108. The longitudinal rod 108 may freely rotate within the aperture 118. An adjustment member 120 may adjust a clamping force provided by the upper portion 114 and the lower portion 116 of the node 106 on the end portion 110.

Figure 5A:
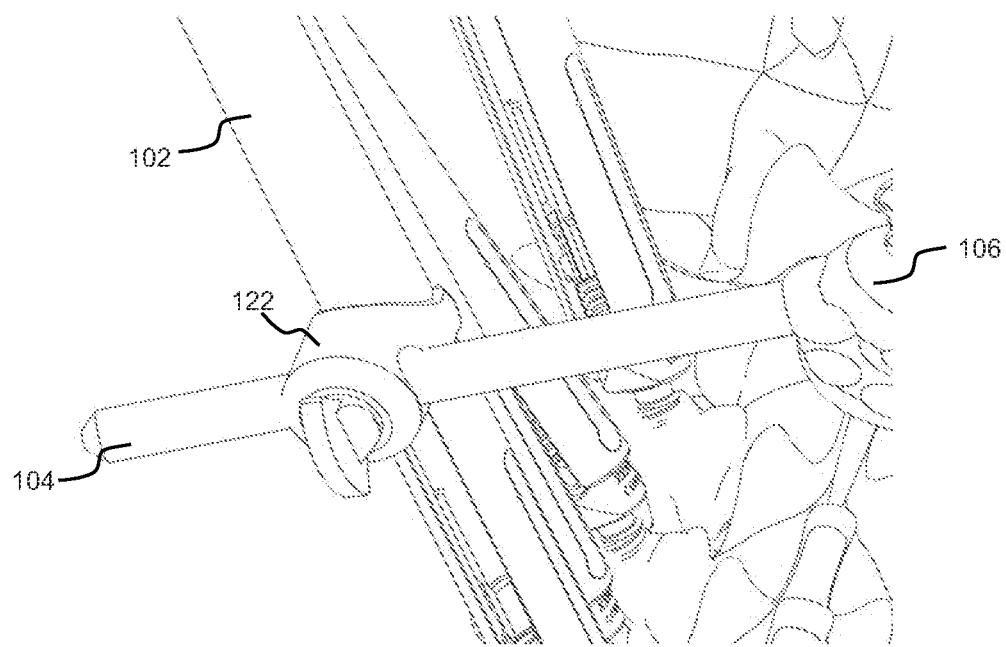
FIGS. 5A and 5B are perspective views of an exemplary linking member of the system for correcting spinal deformities according to the principles of the present disclosure.
Figure 5B:
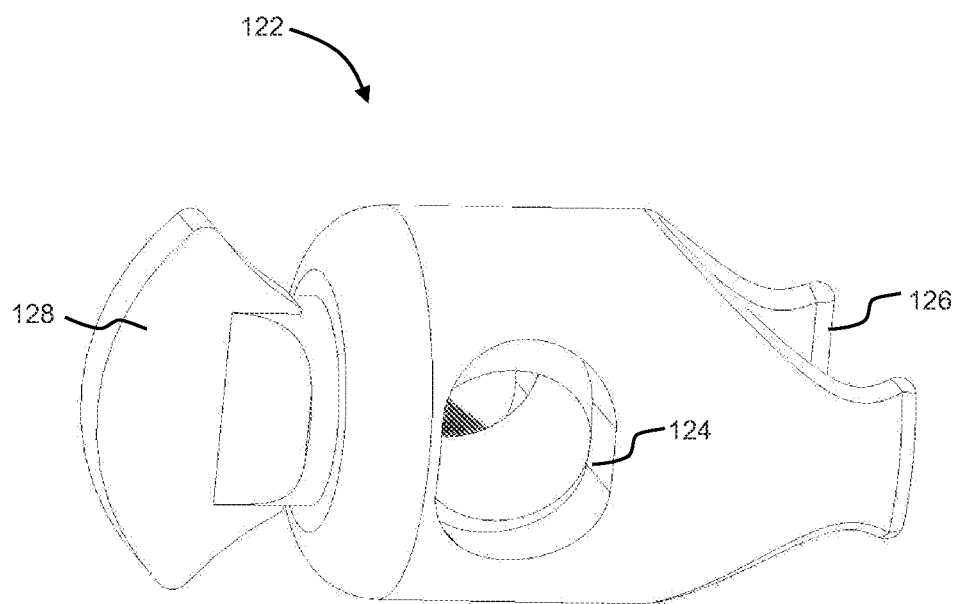

Each node 106 adjustably connects the longitudinal rod 108 to the transverse rods 104. Several nodes 106 may be joined together, or in pairs, or any other desired quantity. By joining segments of nodes 106 and transverse rods 104, the nodes 106 can rotate to accommodate differing anatomy for each level of vertebrae. As shown in FIG. 5A, the transverse rod 104 connects the extension member 102 to the alignment nodes 106. For example, a linking member 122, as shown also in FIG. 5B, may include a first transverse aperture 124 for receiving the transverse rod 104. The linking member 122 may include a second extension member aperture 126 for coupling with the extension member 102. A lock 128, such as a toggle screw, may lock the linking member 122 along any portion of the extension member 102 as desired. The linking members 122 may be moved along the extension member 102 and also allow for the adjustable attachment of the transverse rods 104 onto the construct. The extension members 102 may be moved in any desirable locked configuration by loosening the adjustment member 120 on the node 106 and the lock 128 on the linking member 122. In another embodiment, the transverse rods 104, nodes 106, linking members 122, and longitudinal rod 108 may join multiple extension members 102. For example, after the extension members 102 are attached to the pedicle screws, the remainder of the construct may be attached to multiple extension members 102.

Figure 6A:
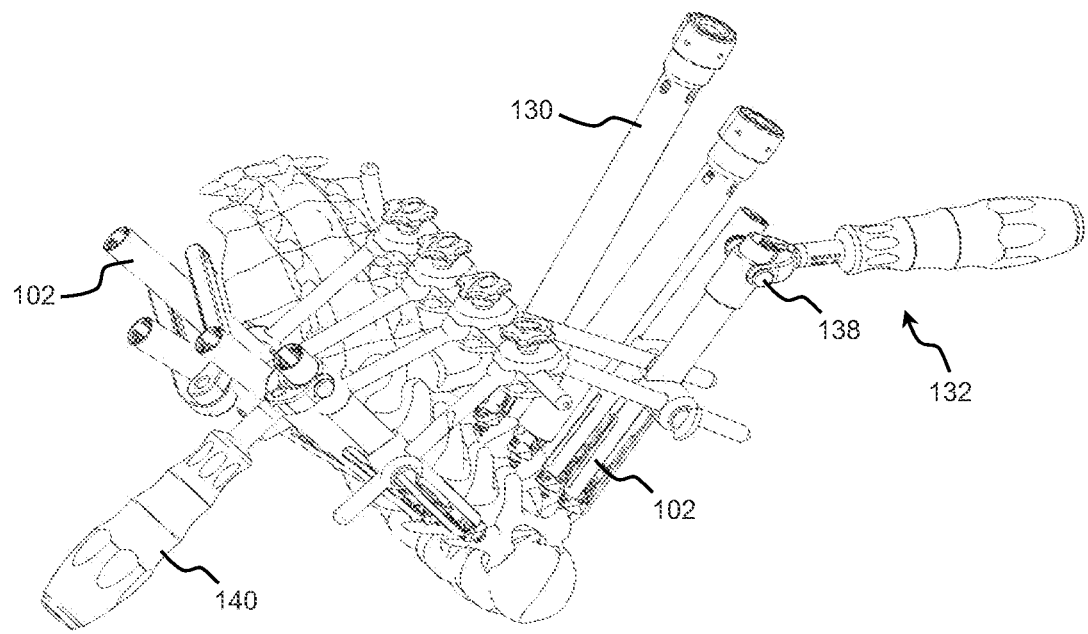
FIGS. 6A and 6B are perspective views of exemplary instruments associated with the system for correcting spinal deformities according to the principles of the present disclosure.
Figure 6B:
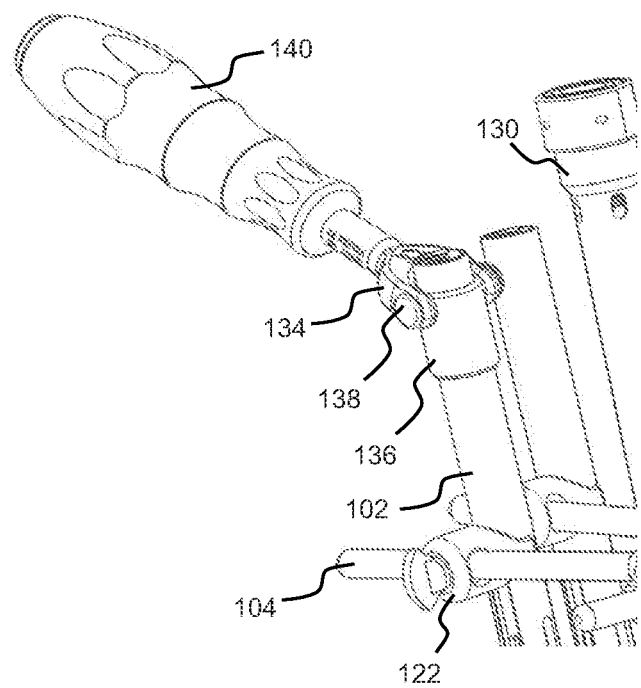

In FIGS. 6A and 6B, additional tubes 130, such as rod reducer tubes, derotation tubes, and the like, may be inserted over the extension members 102 as needed during a deformity correction procedure. For example, the system 100 may include a rod reducer tube to aid in the insertion of the fixation rod into the pedicle screws by persuading the fixation rod into the head of the screw. The system 100 may be configured to accommodate any of screw extenders, derotation tubes, and rod reducer tubes.

Various instruments, such as derotation instruments 132, may removably attach to the extension members 102 and or additional tubes 130 to allow the surgeon to grasp and manipulate the joined extension members 102. In one embodiment, the instrument 132 includes a u-shaped distal end 134 connected to a hollow sleeve 136 which rotates on pins 138 protruding from either side of the distal end 134. The hollow sleeve 136 can be attached to the extension member 102 in any desirable manner and released by a trigger or other similar mechanism. In one particular embodiment, the sleeve 136 can be attached to the extension member 102 by sliding the sleeve 136 onto the proximal end of the extension member 102. The surgeon may use a handle 140 to manipulate the extension member 102 as required to rotate and align the spinal column.

Figure 7A:
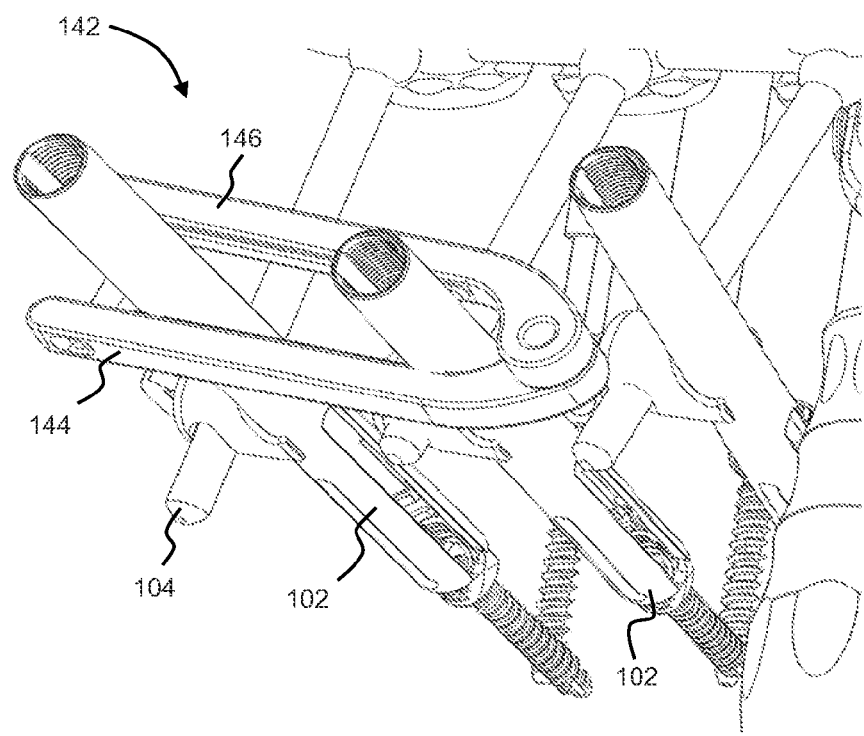
FIGS. 7A and 7B illustrate an exemplary alignment clip of the system for correcting spinal deformities according to the principles of the present disclosure.
Figure 7B:
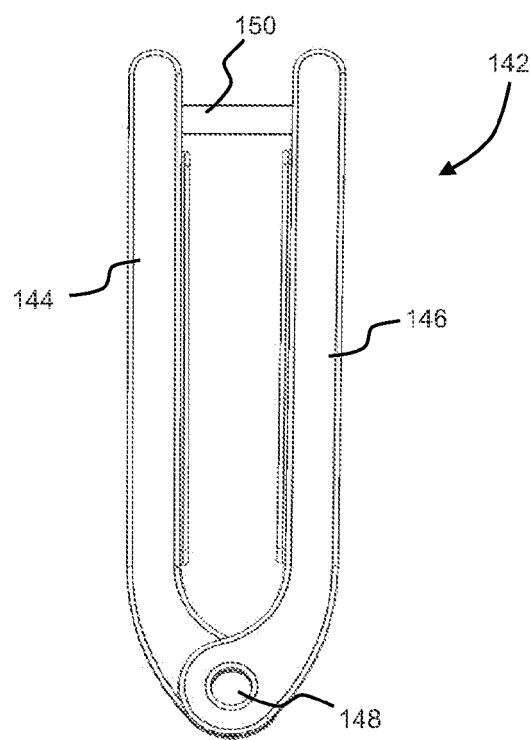
Figure 8A:
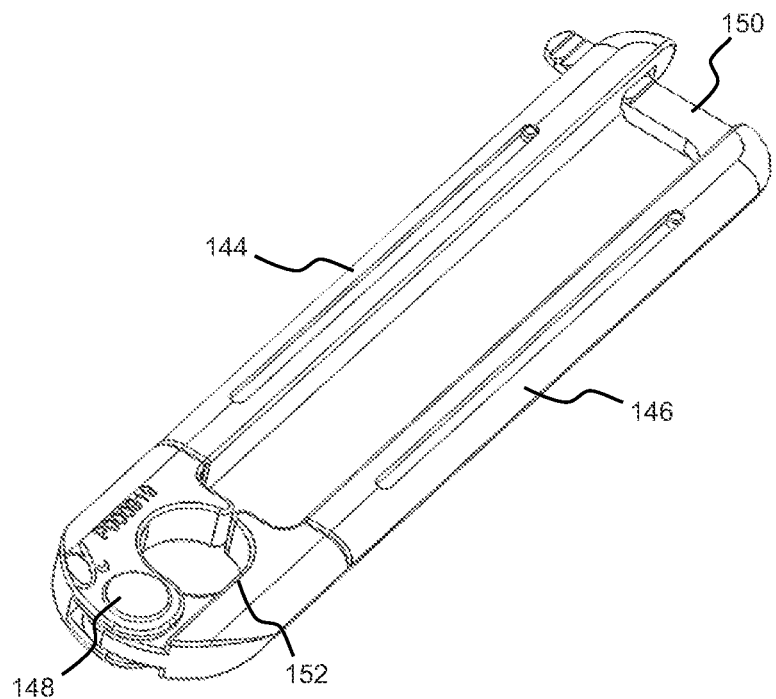
FIGS. 8A and 8B illustrate another exemplary alignment clip and an inter-level connector of the system for correcting spinal deformities according to the principles of the present disclosure.
Figure 8B:
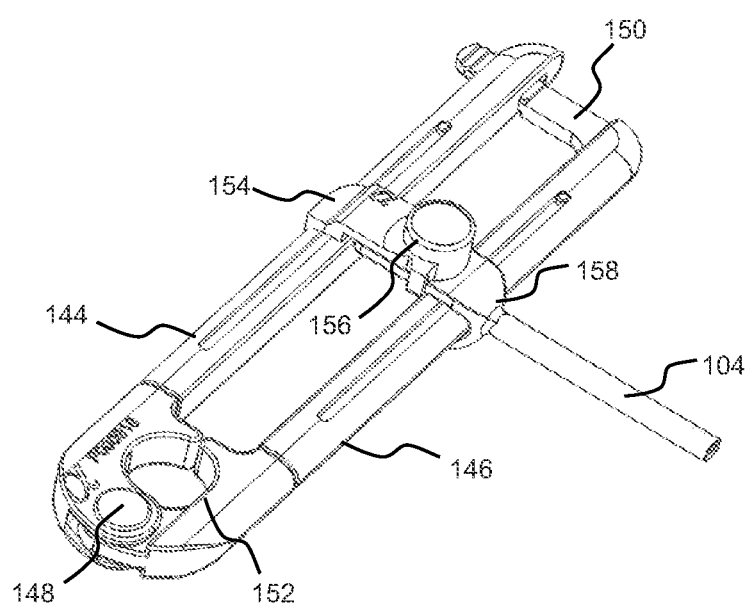

Occasionally, it may be beneficial to move multiple levels of vertebrae in unison to facilitate proper alignment. The system 100 may include an alignment clip 142, as shown in FIGS. 7A and 7B, to connect at least two extension members 102 together for simultaneous manipulation. The clip 142 may include two arms 144 and 146 linked by a pin 148. The arms 144 and 146 spread apart to be inserted around the extension members 102. In one embodiment the clip 142 is clamped around the extension members 102 and closed with a rack and pawl locking mechanism 150. In some embodiments, the clip 142 can be scalloped to better conform to the external shape of the extension member 102. In another embodiment, the clip 142 can have a non-slip surface such as rubber to better grip the extension member 102. In yet another embodiment, as shown in FIGS. 8A and 8B, the clip 142 may include an extension member aperture 152 that receives a first of the extension members 102 for building up a complete system 100. The opening 152 may rigidly secure the clip 142 to the first extension member before connecting with a second extension member.

Figure 9A:
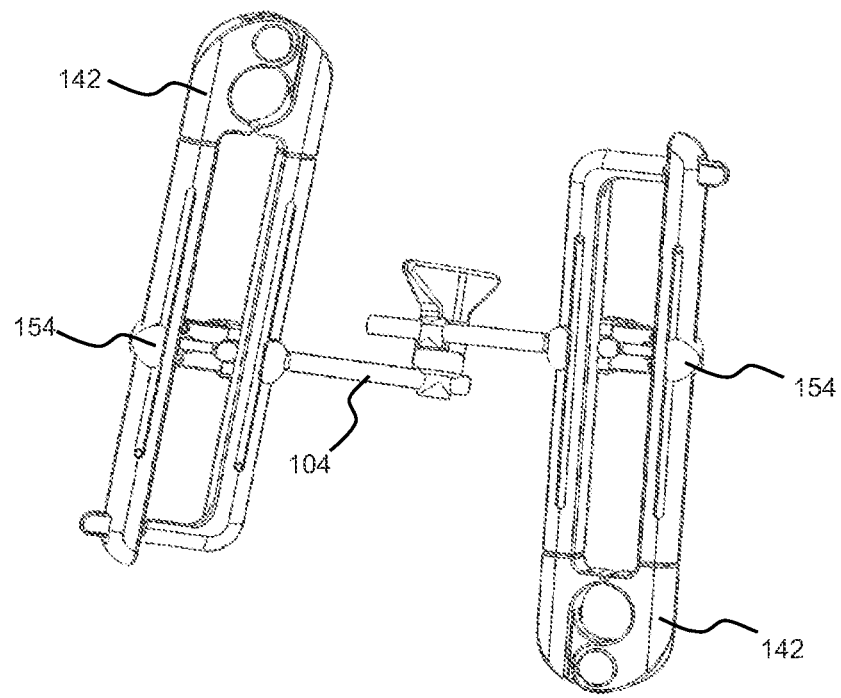
FIGS. 9A and 9B illustrate positioning of the alignment clips and inter-level connectors with the screw extender system according to the principles of the present disclosure.
Figure 9B:
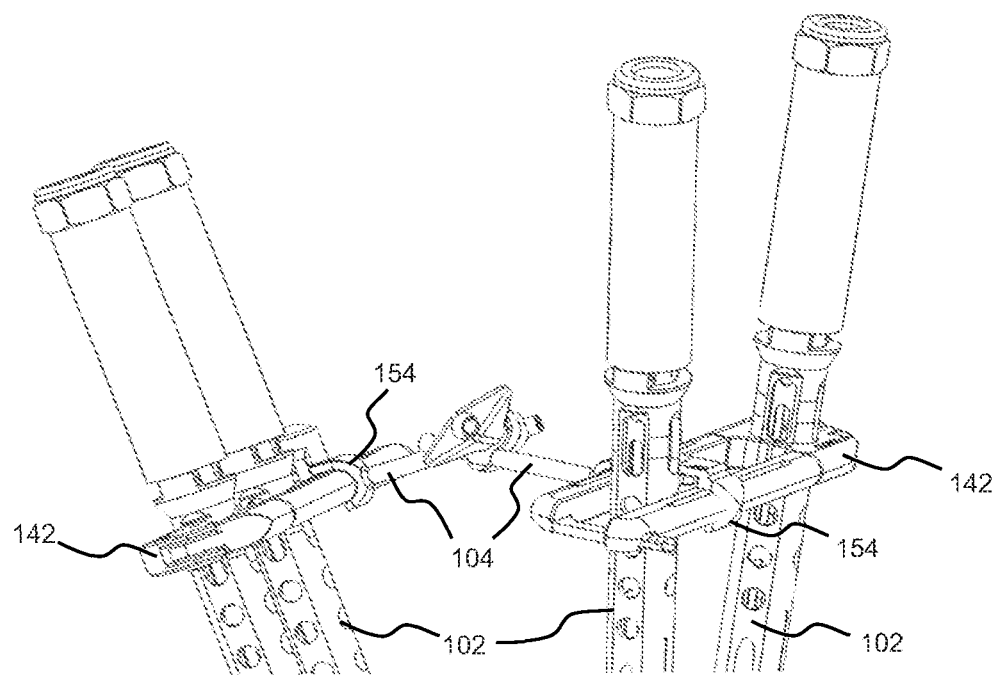

Sometimes, it may be beneficial to couple a transverse rod 104 at a point between two levels of adjacent vertebrae, and thus, between two adjacent extension members 102. FIG. 8B illustrates an inter-level connector 154 that may expand around two arms 144 and 146 of the clip 142. The inter-level connector 154 couples at any point along the two arms 144 and 146 as shown in FIG. 9A. The inter-level connector 154 may be secured to the clip 142 by any of a rack and pawl mechanism, a ratcheting mechanism, or other known coupling mechanism 156. For example, the coupling mechanism 156 may expand the connector 154 wider than the two arms 144 and 146 to release from the clip 142. The coupling mechanism 156 may contract the connector 154 around the two arms 144 and 146 to attaché to the clip 142. The connector 154 may be integral with the transverse rod 104. Alternatively, the connector 154 may attach to the transverse rod 104 with a second attachment mechanism 158 such as threading, a push pin lock, or other known mechanisms for locking rods. Thus, as illustrated in FIG. 9B, the inter-level connector 154 permits placement of transverse rods 104 between adjacent levels of vertebrae and corresponding extension members 102.

Figure 10:
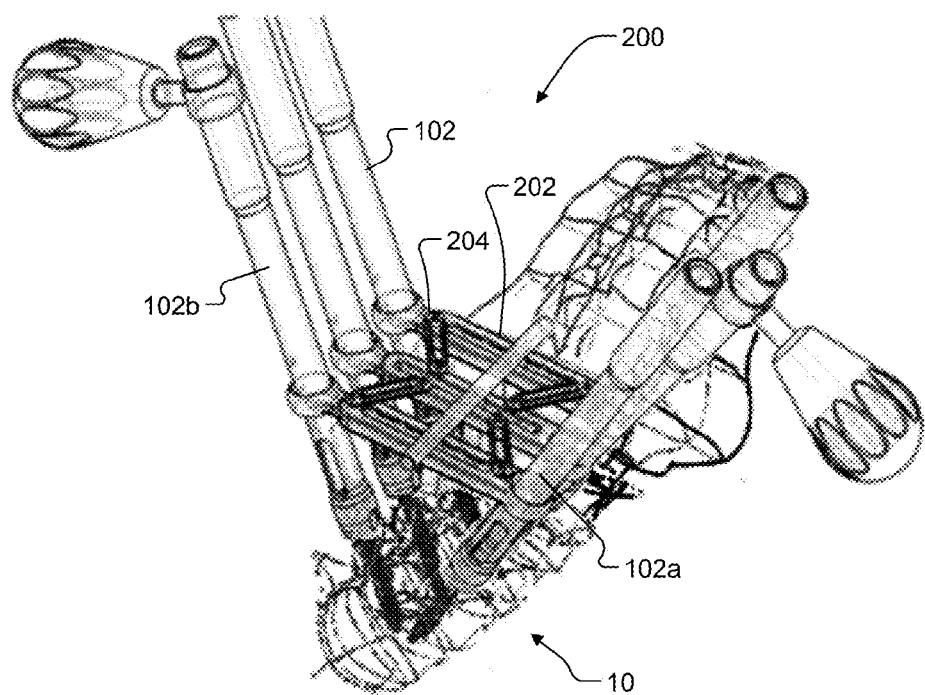
FIG. 10 is a perspective view of another example of a system for correcting spinal deformities as attached to the screw extender system according to the principles of the present disclosure.
Figure 11:
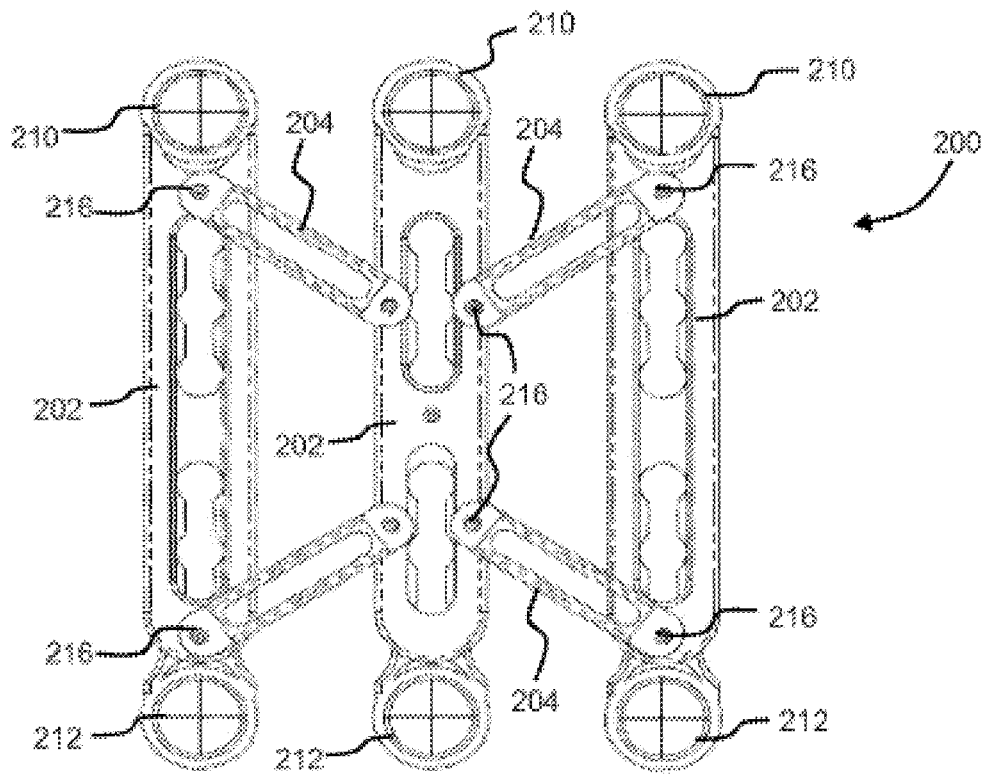
FIG. 11 is a top view of the system for correcting spinal deformities according to the principles of the present disclosure.
Figure 12:
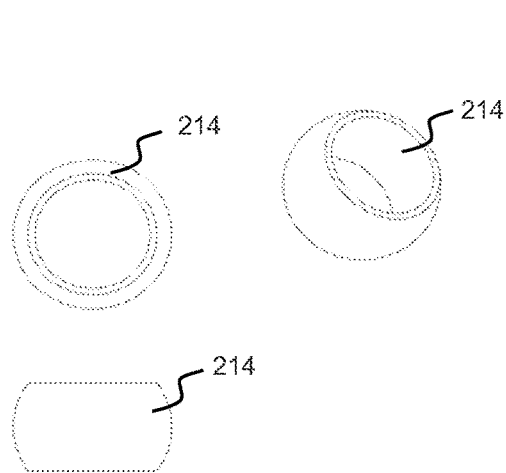
FIG. 12 is a sleeve of the system for correcting spinal deformities according to the principles of the present disclosure.
Figure 13:
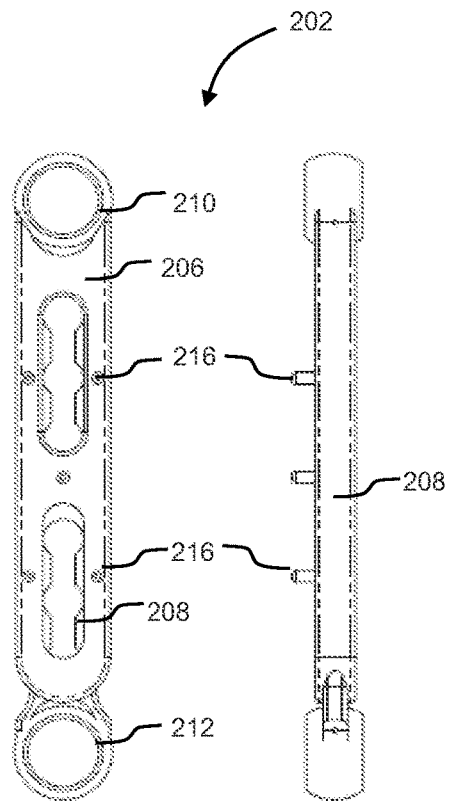
FIG. 13 is a portion of the system for correcting spinal deformities in an unexpanded position according to the principles of the present disclosure.
Figure 14:
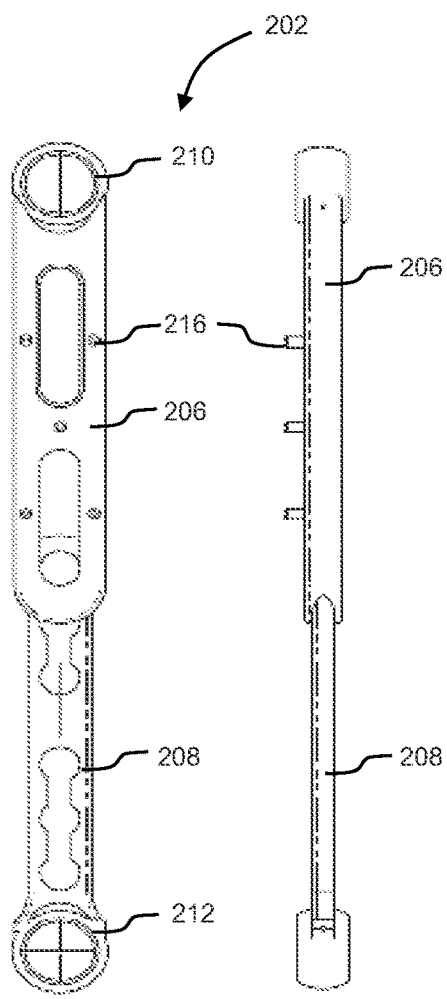
FIG. 14 is the portion of the system for correcting spinal deformities in an expanded position according to the principles of the present disclosure.

FIGS. 10-14 illustrate another embodiment of a system 200 for alignment of the spine 10 that may be used with one or more screws installed in the pedicles of the vertebral bones. As shown in FIG. 11, the system 200 comprises expandable transverse links 202 and linking arms 204. Each transverse link 202 may include a first plate 206 and a second plate 208 as shown most clearly in FIG. 14 The first plate 206 may include a first extension member aperture 210 for connection with a first one of the extension members 102a. The second plate 208 may include a second extension member aperture 212 for connection with a second one of the extension members 102b extending from an opposite side of the same vertebra. The first plate 206 and second plate 208 slide relative to one another to enable variable positioning along the height of the extension members 102. For example, the transverse link 202 may include an unexpanded configuration shown in FIG. 13 and an expanded configuration shown in FIG. 14. A sleeve 214, as shown in FIG. 12, may be disposed within the apertures 210 and 212 to facilitate various angles formed by the intersection of the transverse link 202 and the extension member 102. The sleeve 214 may form a generally spherical shape and pivot about the apertures 210 and 212 as a ball and socket joint. For example, the apertures 210 and 212 may include rounded inner surfaces corresponding to the spherical shape of the sleeve 214.

Continuing with FIGS. 10-14, the transverse links 202 may include attachment points 216 such as pins, pegs, and the like, for attachment with mating features of the linking arms 204. In the present example, the linking arms 204 include mating features such as apertures and slots 218. The attachment points 216 allow the linking arm 104 to pivotally attach to the transverse links 202. Additionally, the linking arm 204 can swivel about the attachment point 216 thereby adjusting its position in relation to the transverse links 202.

As shown in FIG. 10, in one embodiment, a desired number of extension members 102 are connected to the vertebrae by attaching to a corresponding number of bone screws. The system 200 may subsequently be attached to the extension members 102. The surgeon may pre-assemble the system 200 or add one component at a time connecting the desired number of transverse links 202 with linking arms 204 as required to properly align the spine 10. If one link 202 is added at a time, each sleeve 214 is attached to the proximal end of the extension member 102 connected to the same vertebra thereby spanning the space perpendicular to the spine. Second and subsequent transverse links 202 can be added to the system 200 with sleeves 214 attached to the proximal ends of the adjacent extension members 102. Linking arms 204 may be added between the transverse links 202 to connect each adjacent transverse link 202 to all other links 202 of the system 200.

Once the entire system 200 is assembled, the linking arms 204, plates 206 and 208, and the extension members 102 are capable of movement as one unit. Each transverse link 202 is additionally and separately lockable in its individual expanded position allowing one link 202 to be adjusted while the others remain static. After the vertebrae have been manipulated into their desired positions during the derotation procedure, the position can be secured by inserting a fixation rod into the multiple extension members 102. The rod is inserted parallel to the spine, and secured in the bone screw with a set screw. One example of the rod and set screw placement is described in U.S. Patent Pub. No. 2010/0036443. After the rods are secured, the system 200 can then be disassembled and the surgery completed.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. A system for correcting spinal deformities of the vertebrae using a first and a second extension member, the first and the second extension members each haw having an upper and a lower portion and are configured to attach to a respective pedicle screw, comprising:
   a first transverse link and a second transverse link, wherein each of the first transverse link and the second transverse includes a first plate and a second plate and a plurality of attachment points, the first plate having a first aperture disposed on a distal end of the first plate, the second plate having a second aperture disposed on a distal end of the second plate, wherein the first and second apertures are circular, the first plate configured to receive the second plate so as to vary a first adjustable length of the first transverse link and the second transverse link;
   a first sleeve having a spherical outer surface so as to pivot freely in three dimensional space within the first aperture of the first plate, the first aperture being concentric to the first sleeve, wherein the first sleeve is concentric to the first extension member so as to receive the first extension member at a first plurality of angles and a second sleeve having a spherical outer surface so as to freely pivot in three dimensional space within the second aperture of the second plate, the second aperture being concentric to the second sleeve, wherein the second sleeve is concentric to the second extension member so as to receive the second extension member at a second plurality of angles;
   a first linking arm having a first end opposite a second end, wherein the first and second ends are pivotably attached to a respective attachment point of the first and second transverse links so as to allow for a radial displacement of the first transverse link relative to the second transverse link; and
   a second linking arm being of equal length to the first linking arm, the second linking arm having a first end opposite a second end, wherein the first and second ends are pivotably attached to a respective attachment point of the first and second transverse links so as to allow for a lateral displacement of the first transverse link relative to the second transverse link.

2. The system of claim 1, wherein the first plate includes an elongated slot configured to slidably receive the second plate within the first plate to vary the first adjustable length.

3. The system of claim 1, wherein each of the first and second apertures includes a generally concave inner surface so as to freely rotatably receive respective first and second sleeves.

4. The system of claim 1, wherein the plurality of attachment points is a pin.

5. The system of claim 1, further including a third transverse link having a first plate and a second plate and a plurality of attachment points, the first plate having a first aperture disposed on a distal end of the first plate, the second plate having a second aperture disposed on a distal end of the second plate, wherein the first and second apertures are circular, the first plate configured to receive the second plate so as to vary a first adjustable length of the first transverse link and the second transverse link;
   a third linking arm having a first end opposite a second end, wherein the first and second ends are pivotably attached to a respective attachment point of the second and third transverse links so as to allow for the radial displacement of the second transverse link relative to the third transverse link.

* * * * *